United States Patent [19]

Hodgson, Jr.

[11] 4,366,158
[45] Dec. 28, 1982

[54] 1-(8-QUINOLYL)-2-PYRROLIDONE AND ITS PHARMACEUTICAL COMPOSITIONS

[75] Inventor: Gordon L. Hodgson, Jr., Durham, N.C.

[73] Assignee: Burroughs Wellcome Co., Research Triangle Park, N.C.

[21] Appl. No.: 209,426

[22] Filed: Nov. 24, 1980

[30] Foreign Application Priority Data

Nov. 30, 1979 [GB] United Kingdom ................. 7941409

[51] Int. Cl.³ ..................... A01K 31/47; C07D 419/04
[52] U.S. Cl. ..................................... 424/258; 546/171
[58] Field of Search ................. 546/162, 171; 424/258

*Primary Examiner*—David B. Springer
*Attorney, Agent, or Firm*—Donald Brown

[57] ABSTRACT

The compound of formula (I)

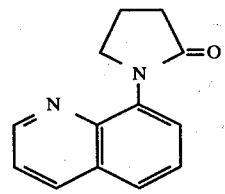

(I)

and acid addition salts thereof are of value in medicine in the treatment or prophylaxis of pain, inflammation or fever. The compound and its salts may be administered alone or as a pharmaceutical formulation. The compound may be prepared by methods analogous to those known in the art or, for example, by cyclization of a 4-halo-N-(8-quinolyl)butyramide in the presence of aqueous sodium hydroxide and a phase transfer catalyst such as triethylbenzyl ammonium chloride.

5 Claims, No Drawings

1-(8-QUINOLYL)-2-PYRROLIDONE AND ITS PHARMACEUTICAL COMPOSITIONS

This invention relates to a compound useful in medicine, to the synthesis of the compound, to pharmaceutical formulations containing the compound or a salt thereof and the preparation of such formulations, and to the use of the compounds in medicine.

We have found that the compound of formula (I),

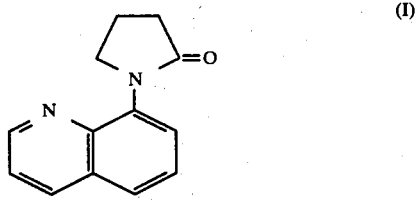

which is chemically named 1-(8-quinolyl)-2-pyrrolidinone, and acid addition salts thereof are of value in medicine in the treatment or prophylaxis of pain, inflammation or fever.

Any reference hereinafter to the compound of formula (I) shall be taken to include reference to the acid addition salts thereof.

The compound of formula (I) has been found to have analgesic activity as shown by the acetic acid writhing assays (Koster et al., Proc Soc Exp Biol Med, 18, 412 (1959); Vinegar et al., Handbook of Experimental Pharmacology, 50-2; ch. 26, Anti-inflammatory Drugs, Ed. J. R. Vane and S. H. Ferreira (1978)) and a modification of the trypsin hyperalgesic assay (Vinegar et al., Eur J Pharmacol 37, 23 (1976)). In this respect the compound of formula (I) is like acetaminophen but different from aspirin which is inactive in the former assay. In addition, the analgesic activity of the compound of formula (I) is believed to be unlike that of morphine or codeine since its analgesic activity is not inhibited by naloxone; it is inactive when injected directly into the brain; and it does not appreciably bind to the morphine receptor.

The compound of formula (I) has also been found to have potent, long-lasting acute anti-inflammatory activity in the rat as shown in the carrageenin pleurisy assay (Vinegar et al., Proc Soc Exp Biol Med 151, 556, (1976)) and in the carrageenin hindlimb oedema assay (Winter et al., Proc Soc Exp Biol Med, 111, 544–547, (1962); Vinegar et al., J. Pharmacol Exp Ther, 166, 96–103 (1969)). The compound of formula (I) also does not inhibit prostaglandin cyclooxygenase, peroxidase or lipoxygenase and is therefore not believed to be an 'aspirin-like' anti-inflammatory compound. The compound of formula (I) resembles acetaminophen in its anti-inflammatory action but it has been found to be more potent and to have a longer lasting anti-inflammatory effect.

The compound of formula (I), like acetaminophen, has also been found to have antipyretic and hypothermic activity as shown by the yeast-induced hyperthermia assay in the rat (Khalili-Varasteh et al., Arch Int Pharmacodyn, 219, 149-159 (1976)). That is to say, the compound of formula (I) combats fever in the rat at low dose levels and lowers the body temperature of rats with a 'normal' temperature at higher dose levels.

The differences between the modes of action of the compound of formula (I) so far evaluated and those of previously described anti-inflammatory, analgesic or antipyretic agents imply that the compound of formula (I) may possess a unique pharmacological profile.

The compound of formula (I) is readily soluble in, for example, water and 0.1 N HCl, the base having a solubility of greater than 50 mg/ml in both the aforementioned solvents.

When used in medicine, the salts of the compound of formula (I) should be both pharmacologically and pharmaceutically acceptable acid addition salts, but non-acceptable salts may conveniently be used to prepare the base or acceptable salts of the base, and are not excluded from the scope of this invention. Such pharmacologically and pharmaceutically acceptable salts include, but are not limited to, those prepared from the following acids: hydrochloric, hydrobromic, sulphuric, nitric, phosphoric, oxalic, maleic, salicylic, toluene-p-sulphonic, tartaric, citric, methanesulphonic, formic, malonic, naphthalene-2-sulphonic and benzenesulphonic.

A compound of formula (I) and its salts may be prepared by any method known in the art for the preparation of compounds of analogous structure.

(1) A method for preparing a compound of formula (I) comprises cyclisation, as hereinafter described, of a compound of formula (II) or a compound of formula (III):

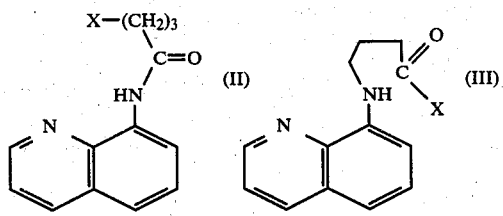

wherein X is a standard leaving group (J. March, Advanced Organic Chemistry, 2nd Ed., page 187, New York (1977)) such as halide for example chloride or bromide, hydroxide, —$OR^1$, imidazolyl, sulphoxonium or tosyl; and $R^1$ is hydrogen or alkyl of 1 to 4 carbon atoms, preferably ethyl. Preferred compounds of formula (II) are those wherein the leaving group is a halide (such as chloride or bromide), hydroxide or tosyl, and preferred compounds of formula (III) are those wherein the leaving group is —$OR^1$ as defined. A particularly preferred method comprises cyclisation of a compound of formula (II) as hereinbefore defined, especially wherein X is chloride.

Cyclisation may be effected at room temperature or with heating for example at a temperature of 155°–220° C., optionally in an oxygen-free atmosphere for example in nitrogen, optionally in an inert solvent such as tetrahydrofuran, dichloromethane, diethyl ether, tert-butanol, xylenes, or toluene, and optionally with a catalyst. The catalyst chosen will depend on the compound of formula (II) or (III) to be cyclised, for example, where the reaction involves elimination of an acid such as hydrochloric, a basic catalyst may be used with or without a solvent such as water or an alcohol such as butanol optionally, but preferably, in the presence of a phase transfer catalyst such as triethylbenzyl ammonium chloride with or without a solvent such as dichloromethane, diethyl ether, xylenes or toluene, but preferably dichloro methane. Examples of suitable basic catalysts are: an alkali metal hydride, hydroxide or alkoxide such as potassium or sodium hydride, potassium or sodium hydroxide, potassium tert-butoxide or lithium di-isopropylamide. The most preferred method of cyclisation is effected by using aqueous sodium hydroxide in the presence of triethylbenzyl ammonium chloride at room temperature.

Where X is a slow or poor leaving group cyclisation may take place by conversion in situ to a further or better leaving group. For example where X is hydroxide, tosyl chloride may be present in the reaction mixture in order that the tosyloxy group (a better leaving group) is substituted for the hydroxide group thereby causing cyclisation to proceed faster and more completely.

(2) A further method comprises reduction of a corresponding oxidised precursor of a compound of formula (I). For example, reduction of N-(8-quinolyl)succinimide (formula (IV)):

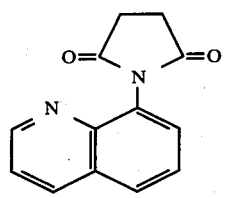

(IV)

The reducing agent employed may be selected from those known to persons skilled in the art, such as lithium aluminium hydride, di-iso-butyl aluminium hydride or a lithium trialkyl hydride where the alkyl moiety has from one to four carbon atoms, and sodium borohydride in dilute mineral acid for example hydrochloric acid.

A compound of formula (II), (III) or (IV) may itself be prepared by analogous methods known to those skilled in the art, for example, by reacting 8-aminoquinoline (formula (V)):

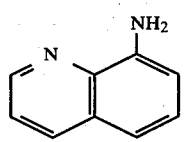

(V)

or a salt thereof such as an acid addition salt thereof for example the hydrochloride or an alkali metal or alkaline earth metal salt thereof for example the lithium salt, with an internal ester, acid halide for example acid chloride, or acid anhydride. For example, the compound of formula (V) maybe reacted with Cl—(CH$_2$)$_3$—COCl to produce a compound of formula (II) wherein X is chloride in the presence of triethylamine in dimethoxyethane or dichloromethane.

The reaction may be carried out under the same or similar conditions as described hereinabove for cyclisation since the compound of formula (II) or (III), or the corresponding open-chain precursor of the compound of formula (IV), need not be isolated but may be cyclised in situ, for example by a method analogous those described by A. Pernot and A. Willemart in Memories Presentes a La Soc Chim 324 (1953); W. R. Schleigh, A. Catala and F. D. Popp in J Het Chem, 2, 379 (1965); or I. Badilescu in Tetrahedron, 26, 4207 (1970).

(3) A further method comprises the oxidation and/or dehydrogenation of a correspondingly reduced or hydrogenated precursor of a compound of formula (I).

For example, by dehydrogenation of a tetrahydro- or dihydro-1-(8-quinolyl)-2-pyrrolidinone (formula (VIA) or formula (VIB)):

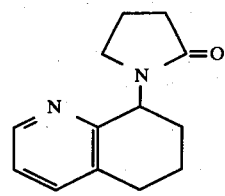

(VIA)

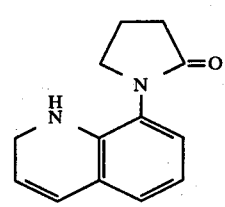

(VIB)

Oxidation or dehydrogenation may be effected by methods known to those skilled in the art, for example, by bubbling oxygen through the reactant with or without a base such as tert-butyl lithium; by heating with sulphur, arsenic acid, or with nitrobenzene, cyclohexane or cyclohexadiene optionally in the presence of a catalyst for example palladium on carbon or with a quinone for example tetrachloroquinone, or in the presence of a metal catalyst such as a noble metal or other suitable metal for example platinum, palladium or copper chromite and an inert solvent such as xylene.

A compound of formula (VIA) may itself be prepared by methods known in the art, for example, by a Diels Alder reaction between 3-vinylpyridine (formula (VII)) and N-vinylpyrrolidinone (formula (VIII)):

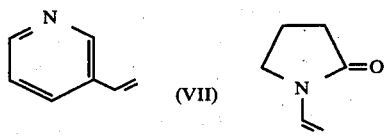

(VII)  (VIII)

A compound of formula (VIB) may itself be prepared by methods known in the art for the synthesis of quinoline and its derivatives, for example a modified Skraup reaction between acrolein and 1-(2-aminophenyl)-2-pyrrolidinone (formula (IX)):

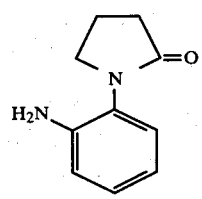

(IX)

(4) A further method comprises concurrently methylating and cyclising N-(8-quinolyl)acrylamide (formula (X)):

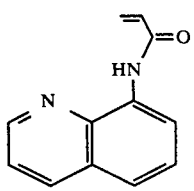

(X)

with a suitable methylating agent such as trimethyl sulphoxonium iodide in a manner analogous to the method described by Metzger et al. in Angew. Chem. Int. (1963) 2 (10), 624.

(5) A further method comprises hydrolysis of 1-(8-quinolyl)-2-imino-pyrrolidine (formula (XI)):

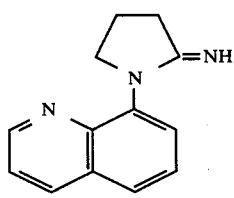

(XI)

The hydrolysis may be effected by standard hydrolysing agents known to those skilled in the art, for example, by adding a few drops of water or dilute aqueous acid to the compound.

The compound of formula (XI) may itself be prepared according to the method described by Kwok et al. in J. Org. Chem. (1967) 32, 738.

(6) A further method comprises a displacement reaction between a compound of formula (XII) and the pyrrolidinone anion (formula (XIII):

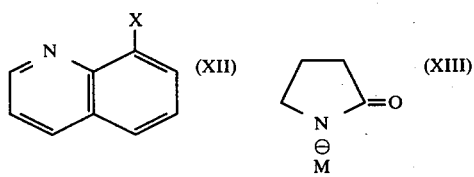

wherein X is a standard leaving group such as those hereinbefore described and M is an alkali metal or alkaline earth metal cation such as $Na^+$.

A compound of formula (I) or pharmaceutically acceptable acid addition salts thereof (hereinafter referred to as the active compound) may be used in the relief, treatment or prophylaxis of pain, inflammation or fever, in a mammal, including man, such as: that resulting from headache, toothache, pain following general dental procedures, oral and general surgery, dysmenorrhea, myalgia, pain of unresectable cancer, joint and peripheral nerve disorders, rheumatoid arthritis, rheumatoid spondylitis, osteoarthritis, gouty arthritis and other arthritic conditions, pyresis and other conditions associated with pain, inflammation and fever.

The amount of the active compound required for use in the above conditions will, of course, vary both with the route of administration, the condition under treatment, and the mammal undergoing treatment, but is ultimately at the discretion of the physician. However, a suitable analgesic, anti-inflammatory and/or antipyretic dose of the active compound for a mammal is in the range of from 3 to 120 mg per kilogram bodyweight per day; a typical dose for a human recipient being 15 mg/kg body weight per day.

Unless otherwise indicated all weights are calculated as the base of formula (I): for acid addition salts thereof the figures would be increased proportionately. The desired dose is preferably presented as between two and four sub-doses administered at appropriate intervals throughout the day. Thus where three sub-doses are employed each will lie in the range of from 1 to 40 mg (base)/kg body weight; a typical dose for a human recipient being 5 mg (base)/kg body weight.

While it is possible for the active compound to be administered alone as the raw chemical, it is preferably to present the active compound as a pharmaceutical formulation. Formulations of the present invention, both for veterinary and for human medical use, comprise the active compound together with one or more pharmaceutically acceptable carriers therefor and optionally any other therapeutic ingredients. The carrier(s) must be 'pharmaceutically acceptable' in the sense of being compatible with the other ingredients of the formulation and not deleterious to the recipient therefor. The other therapeutic ingredient(s) may include caffeine or other analgesics, anti-inflammatories or antipyretics such as aspirin and codeine.

The formulations include those suitable for oral, rectal or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound; as a powder or granules; or as a solution or a suspension in an aqueous liquid or non-aqueous liquid such as a syrup, an elixir or a draught, or as an oil-in-water emulsion or water-in-oil emulsion. The active compound may also be presented as a bolus, electuary or paste.

A tablet may be made by compression or moulding, optionally with one or more accessory ingredients. Compressed tablets may be prepared by compressing in a suitable machine, the active compound being in a free-flowing form such as a powder or granules, optionally mixed with a binder, lubricant, inert diluent, surface active or dispersing agent. Moulded tablets may be made by moulding in a suitable machine, comprising a mixture of the powdered active compound with any suitable carrier.

A syrup may be made by adding the active compound to a concentrated, aqueous solution of a sugar for example sucrose to which may also be added any accessory ingredient. Such accessory ingredient(s) may include flavourings, an agent to retard crystallization of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

It will be understood from the foregoing description that what we shall claim in accordance with this invention may comprise any novel feature described herein, principally but not exclusively for example:

(a) the compound of formula(I) chemically named 1-(8-quinolyl)-2-pyrrolidinone or an acid addition salt thereof;

(b) a method as hereinbefore described for the preparation of the compound of formula (I) or an acid addition salt thereof, together with the compound when so prepared;

(c) a compound of formula (II), (III), (IV), (X) or (XI) and a method for the preparation thereof;

(d) a pharmaceutical formulation comprising the compound of formula (I) or a pharmaceutically acceptable acid addition salt thereof together with a pharmaceutically acceptable carrier therefor;

(e) a method for the preparation of a formulation of the compound of formula (I) or an acid addition salt thereof, comprising admixture of the active compound as hereinbefore defined with a pharmaceutically acceptable carrier therefor;

(f) a method for the treatment of prophylaxis of pain in a mammal, including man, comprising the administration to said mammal of a non-toxic, effective analgesic amount of the compound of formula (I) or an acid addition salt thereof;

(g) a method for the treatment or prophylaxis of inflammation in a mammal, including man, comprising the adminstration to said mammal of a non-toxic, effective anti-inflammatory amount of the compound of formula (I) or an acid addition salt thereof;

(h) a method for the treatment or prophylaxis of pyresis in a mammal, including man, comprising the administration to said mammal of a non-toxic, effective antipyretic amount of a compound of formula (I) or an acid addition salt thereof; or (i) the compound of formula (I) or an acid addition salt thereof for use in the treatment or prophylaxis of pain, inflammatin or pyresis in a mammal, including man.

The following Examples are provided by the way of illustration of the present invention and should in no way be construed as a limitation thereof. All temperature indicated are in degrees Celsius.

EXAMPLE 1

Preparation of 1-(8-Quinolyl)-2-pyrrolidinone

A solution of 8-aminoquinoline (25 g, 0.17 mole) in γ-butylrolactone (40 ml) was heated (in a dry nitrogen atmosphere) with stirring in a 200° oil bath for 5 days.

The cooled reaction mixture was partitioned between dilute hydrochloric acid and methylene chloride. The aqueous phase was neutralized and extracted with methylene chloride. The organic layers were combined, treated with charcoal, filtered over alumina and CELITE (trade name) filter aid, washed with methylene chloride, and concentrated under reduced pressure. The resulting oil on long-standing at $-19°$ afforded a solid which, on recrystallization (ether/pentane), yielded crude 1-(8-quinolyl)-2-pyrrolidinone. Recrystallization from a methylene chloride/ether/pentane mixture afforded 1-(8-quinolyl)-2-pyrrolidinone, (m.p. 121.5°–122°), yield 5.4%.

Elemental analysis: Calculated for $C_{13}H_{12}N_2O$: C, 73.56%; H, 5.70%; N, 13.20%. Found: C, 73.55%; H, 5.68%; N, 13.08%.

Thin layer chromatography (tlc): 100–200 µg loading on silica gel (EM Reagents), F254 glass plates, developed with chloroform: methanol (95:5) produced one spot at $R_f 0.33$ (lined tank) or $R_f 0.60$ (unlined tank).

Nuclear Magnetic Resonance Spectra (NMR): $^{13}C$ (ppm from TMS in $d^6$-DMSO, integral, assignment): 174.59, 20, C=O; 150.23, 81, C2; 143.63, 9, C8A or C8; 136.48, 100, C4; 136.48, 10, C8a or C8; 128.95; 25, C4a; 128.57. 78, C5; 127.47, 81, C6; 127.28, 56, C7; 121.69, 80, C3. $^1H$ (ppm from TMS in CDCl$_3$, number of peaks, $J_{HZ}$, assignment): 8.91, 4, $J_{2,4}=1.8$, H2; 8.18, 4, H4; 7.78, m, H7; 7.73, m, $J_{5,7}=1.9$, H5; 7.58, m, $J_{6,7}=8.4$ and $J_{5,6}=7.6$, H6; 7.42, 4, $J_{2,3}=4.2$ and $J_{3,4}=8.3$, H3; 4.13, 3, $H_a$; 2.72, m, $J_{a,b}J_{b,c}\approx7.2$, $H_c$; 2.32, m, $H_b$. Values for coupling constants and chemical shifts were obtained from spin simulation.

EXAMPLE 2

Preparation of 1-(8-Quinolyl)-2-pyrrolidinone

Potassium hydride in oil was washed with dry pentane (in a dry nitrogen atmosphere) leaving 2.5 g (0.062 mole) of potassium hydride which was covered with dry tetrahydrofuran (25 ml). To the slurry of potassium hydride (at room temperature) was added dropwise a solution of 8-aminoquinoline (5 g, 0.035 mole) in dry tetrahydrofuran (25 ml), with stirring, followed by addition of dry hexamethylphosphoric triamide (25 ml). After stirring for 1 hour at room temperature, the reaction was cooled in an ice bath and a solution of γ-butyrolactone (2.8 ml, 0.036 mole) in dry tetrahydrofuran (10 ml) was added and the reaction stirred for 1 hour. The reaction was warmed to room temperature and a solution of p-toluenesulphonyl chloride (8 g, 0.042 mole) in dry tetrahydrofuran (10 ml) was added. The reaction was poured into ice water, filtered and the pH was adjusrted to pH 3.5. The product was extracted with methylene chloride and washed with cupric chloride to remove traces of 8-aminoquinoline. The product organics were dried, concentrated under reduced pressure and the residue was crystallized from ether/pentane affording 1-(8-quinolyl)-2-pyrrolidinone, yield 5.4%, which was identical by tlc and NMR in comparison with the product of Example 1.

EXAMPLE 3

Preparation of 1-(8-Quinolyl)-2-pyrrolidinone

A. Preparation of 4-Chloro-N-(8-quinolyl)butyramide

A solution of 8-aminoquinoline (10 g, 0.069 mole) and triethylamine (10 ml, 0.072 mole) in dry tetrahydrofuran (40 ml) was treated dropwise at room temperature with 4-chlorobutyryl chloride (about 0.07 mole) until the green reaction mixture turned yellow in colour. The reaction was filtered and the solids (triethylamine hydrochloride) were washed with tetrahydrofuran. The

B. Carrageenin Hindlimb Oedema Assay (CHOA)

Following the procedure described by Winter et al. in Proc Soc Exp Biol Med, 111, 544–547, (1962) and modified by Vinegar et al. in J Pharmacol Exp Ther 166, 96–103, (1969), the acute anti-inflammatory activity of the compound of formula (I) and certain known anti-inflammatory drugs was found in the rat. The results are shown in Table II.

TABLE II

Results of Acute Anti-inflammatory Activity Assays
All results are expressed as $ED_{50}$ mg/kg.

| Assay | Compound of formula (I) | Aspirin | Acetaminophen |
|---|---|---|---|
| A (CPA) 3 hr. Vol (p.o.) | 20 ± 4.3 | 28 ± 3.2 | 172 ± 22.4 |
| A (CPA) 3 hr. Cells (p.o.) | 37 ± 10.4 | 75 ± 7.5 | 189 ± 48.6 |
| B (CHOA) | 54 ± 31.6 | 145 ± 74.0 | 215 ± 32.3 |

In addition to these results, it was also found that the acute anti-inflammatory activity of the compound of formula (I) as measured in the CPA, administered as 80 mg/kg (p.o.) lasts for 9 hours, while that for acetaminophen as 220 mg/kg (p.o.) lasts for just over 2 hours. This value represents the time (hours) of drug administration prior to the injection of carrageenin in which the inhibition of the 3 hour pleural exudate volume declined to 40%.

EXAMPLE III

Antipyretic Activity

The Yeast-Induced Hyperthermia Assay was used according to the procedure described by Khalili-Varasteh et al. in Arch. Int. Pharmacodyn. 219, 149–159, (1976) to demonstrate the antipyretic activity of the compound of formula (I) and certain known antipyretics in the rat. The results are shown in Table III.

TABLE III

Results of Antipyretic Activity Assay
All results are expressed as $ED_{50}$ mg/kg

| Assay | Compound of formula (I) | Aspirin | Acetaminophen |
|---|---|---|---|
| Rat Yeast Hyperthermia (p.o.) | 22 ± 3.9 | 50 ± 8.1 | 72 ± 8.6 |

EXAMPLE IV

Toxicity Test

Four non-fasted male rats of 160–250 gram body weight was used for each dose level. The compound to be tested was administered by the indicated route and the symptom onset time, the intensity of the effect and the duration during a 4 hour observation period were recorded. The $LD_{50}$ estimation was based on a 7 day observation and was determined by the method of Miller and Tainter (Proc. Soc. Exp. Biol. Med. 57, 261 (1944)).

TABLE IV

Toxicity Data
All results are expressed as mg/kg.

| Assay | Compound of formula (I) | Aspirin | Acetaminophen |
|---|---|---|---|
| $LD_{50}$ (p.o.) | 1650 | 1610 | 2000 |
| No symptom dose (p.o.) | 250 | 10 | 250 |

In addition to the data in Table IV it was found that the compound of formula (I) does not produce gastric damage in the rat after a single oral dose of 200 mg/kg or 5 days of oral dosing at 40 mg/kg whereas a single oral dose of 30 mg/kg aspirin produces ulcers and haemorrhages.

I claim:

1. A compound of the formula (I):

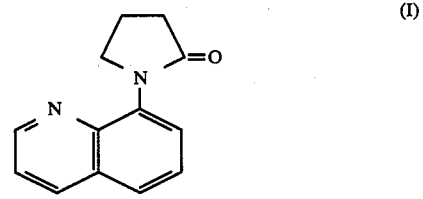

(I)

2. A pharmaceutically acceptable acid addition salt of the compound of claim 1.

3. The hydrochloride salt of claim 2.

4. A pharmaceutical formulation comprising an anti-inflammatory, anti-pyretic or analgesic effective ammount of a compound selected from the group consisting of 1-(8-quinolyl)-2-pyrrolidinone and pharmaceutically acceptable acid addition salts thereof together with a pharmaceutically acceptable carrier therefor.

5. A formulation according to claim 4, selected from a tablet, syrup, suppository and sterile aqueous preparation.

* * * * *

EXAMPLE B—SUPPOSITORY

| Ingredient | Amount per suppository |
|---|---|
| 1-(8-Quinolyl)-2-pyrrolidinone | 325.0 mg |
| Cocoa Butter, q.s. | 2.0 g |
| or Wecobee Base | |

Wecobee is the trade name of a hydrogenated carboxylic acid.

The finely ground active compound was mixed with the melted suppository base (either Cocoa Butter or Wecobee base), poured into moulds and allowed to cool to afford the desired suppositories.

EXAMPLE C—SYRUP

| Ingredient | Amount per 5 ml |
|---|---|
| 1-(8-Quinolyl)-2-pyrrolidinone | 325.0 mg |
| Glycerin | 500.0 mg |
| Sucrose | 3500.0 mg |
| Methylparaben | 5.0 mg |
| Sodium Benzoate | 5.0 mg |
| Cherry Flavour | 0.005 ml |
| Colouring | q.s. |
| Water | q.s to 5.0 ml |

Glycerol, sucrose, methylparaben, and flavouring were combined in 70% of the total batch quantity of water. Sodium benzoate, colouring and the active compound were dissolved in the remaining water, then the two solutions were mixed and clarified by filtration.

EXAMPLE D—TABLET

| Ingredient | Amount per tablet (mg) |
|---|---|
| 1-(8-Quinolyl)-2-pyrrolidinone | 325.0 |
| Lactose | 125.0 |
| Corn Starch | 50.0 |
| Polyvinylpyrrolidone | 3.0 |
| Stearic acid | 1.0 |
| Magnesium stearate | 1.0 |

The active compound was finely ground and intimately mixed with the powdered excipients lactose, corn starch, polyvinylpyrrolidone, magnesium stearate and stearic acid. The formulation was then compressed to afford one tablet weighing 250 mg.

EXAMPLE E—CAPSULE

| Ingredient | Amount per capsule (mg) |
|---|---|
| 1-(8-Quinolyl)-2-pyrrolidinone | 325.0 |
| Lactose | 174.0 |
| Corn Starch | 174.0 |
| Stearic Acid | 2.0 |

The finely ground active compound was mixed with the powered excipients lactose, corn starch and stearic acid and packed into gelatin capsules.

EXAMPLE I

Analgesic Activity

A. Acetic Acid Writhing Test (AAWT)

Using the procedure described by Koster et al. in Fed. Proc. 18, 412 (1959) and Vinegar et al. in Handbook of Experimental Pharmacology, 50-2, ch. 26, Anti-inflammatory Drugs, Ed. J. R. Vane and S. H. Ferreira (1978), the acetic acid writhing test was performed, using both the mouse and the rat, to demonstrate the mild analgesic activity of the compound of formula (I). Comparative results are given in Table I.

B. Trypsin Hyperalgesic Assay (THA)

This assay quantitatively measures analgesia and is designed to be unaffected by compounds possessing anti-inflammatory activity. The procedure described by Vinegar et al. in Eur. J. Pharmacol. 37, 23, (1976) was used to demonstrate the analgesic activity of the compound of formula (I) and of certain known analgesics. The analgesic agents were administered 30 minutes after the administration of trypsin. In addition, a modification of Vinegar's published assay was carried out, comprising the administration of the analgesic agent preceding subplantar injection of trypsin (0.10 ml of 10% solution of trypsin in pyrogen-free water) by 15 minutes. In both THA's, pain scores were determined 60 minutes after trypsin injection. The result of the modification was to increase the sensitivity of the THA to the mild analgesic action of the agents. The comparative results are given in Table I.

In addition to these results, it was found that in the published THA, the analgesic activity of the compound of formula (I) administered as 75 mg/kg (p.o.) lasts for 10.8 hours. This value represents the time (hours) of drug administration, prior to the injection of trypsin, in which the inhibition of hyperalgesia declined to 40%.

TABLE I

Results of Analgesia Assays
All results are expressed as $ED_{50}$ mg/kg.

| Assay | Compound of Formula (I) | Aspirin | Acetaminophen |
|---|---|---|---|
| A (AAWT) (mouse) (p.o.) | 99 ± 9.8 | 137 ± 16.9 | 216 ± 38.4 |
| B (Published THA) (rat) (p.o.) | 37 ± 7.8 | Inactive at 180 | 360 |
| B (Modified THA) (rat) (p.o.) | 13 ± 1.8 | Inactive at 180 | 95 ± 17.2 |
| A (AAWT) (rat) (p.o.) | 22 ± 2.1 | 21 ± 3.4 | 127 ± 16.6 |

EXAMPLE II

Acute Anti-Inflammatory Activity

A. Carrageenin Pleurisy Assay (CPA)

Following the procedure described by Vinegar et al. in Proc Soc Exp Biol Med 151, 556, (1976), the acute anti-inflammatory activity of the compound of formula (I) was compared with that of known anti-inflammatory drugs in the rat. Two assays were performed: in the first, the average 3 hour exudate volume for each drug-treated group was determined and the % inhibition relative to solvent-fed control animals calculated, the $ED_{50}$ being the dose required to reduce the 3 hour exudate volume by 50%; in the second, the number of mobilized neutrophils was quantified and the % inhibition relative to solvent-fed control animals calculated, the $ED_{50}$ being the dose required to reduce the number of neutrophils mobilized at 3 hours by 50%.

solid residue was triturated with ether and the mixture filtered to yield 0.40 g of 1-(8-quinolyl)-2-pyrrolidinone, (m.p. 118°–120°). The ether mother-liquor upon standing gave a second crop of 0.50 g, (m.p. 119°–120°). The combined yield was 1.55 g or 52%.

EXAMPLE 10

Preparation of 1-(8-Quinolyl)-2-pyrrolidinone

8-Aminoquinoline (2.0 g, 13.9 mmol) and ethyl-4-bromobutyrate (2.7 g, 13.9 mmol) were refluxed in 2-methoxyethanol (20 ml) for 71 hours under a nitrogen atmosphere. The progress of the reaction was monitored by tlc (silica gel/diethylether). After one hour, 8-aminoquinoline ($R_f$ 0.79), the intermediate, ($R_f$ 0.88) and a trace of 1-(8-quinolyl)-2-pyrrolidinone ($R_f$ 0.04) were seen. After 71 hours, tlc showed 8-aminoquinoline, a slower moving spot and 1-(8-quinolyl)-2-pyrrolidinone. The solvent was evaporated under vacuum, and the residue was triturated with diethyl ether (50 ml) and decanted. After standing at −5° for 2 days the ether solution deposited crystals of crude 1-(8-quinolyl)-2-pyrrolidinone, (m.p. 109°–118°). The yield was 1 g or 34% and identity was confirmed by tlc and NMR as for Example 1.

EXAMPLE 11

Preparation of 1-(8-Quinolyl)-2-pyrrolidinone

A mixture of 1-(2-aminophenyl)-2-pyrrolidinone (J. Chem. Soc. C, 1969 (10), 1444–8) (3.2 g, 0.018 mole) and arsenic (V) oxide (2.5 g, 0.011 mole) in aqueous sulphuric acid (concentrated sulphuric acid (4.0 ml) in water (1.3 ml)) was heated to 70° and stirred vigorously. Acrolein (2.5 ml, 0.037 mole) was added dropwise at a rate such that the reaction temperature did not exceed 95°. The reaction temperature was maintained at 95° to 115° by heating and stirring in a nitrogen atmosphere for 1 hour after addition of acrolein was complete. The product was poured into water and the pH was adjusted to pH 6 with concentrated ammonia. Extraction of the aqueous solution with methylene chloride, after removal of the solvent, afforded an oil. Separation was achieved by column chromatography (200 g SILICA GEL 60 (Trade Name)). The oil was eluted first with acetone/ethyl acetate (30:70) then acetone/ethyl acetate (50:50) and finally acetone. The solvet was removed from the acetone/ethyl acetate (50:50) and the acetone fractions to afford a homogeneous solid as shown by tlc analysis. Crystallization from acetone afforded 1-(8-quinolyl)-2-pyrrolidinone (m.p. 121°–122°), yield 21%. Analysis of the sample by tlc and NMR as well as elemental analysis verified the identity of this material with that obtained in Example 1.

EXAMPLE 12

Preparation of 1-(8-Quinolyl)-2-pyrrolidinone

A. Preparation of N-(8-quinolyl)-2-propenamide

A solution of 8-aminoquinoline (14.4 g, 0.1 mole) and triethylamine (15 ml, 0.11 mole) in dry tetrahydrofuran (50 ml) was treated dropwise at 0° (under a nitrogen atmosphere) with a solution of acryloyl chloride (8.5 ml, 0.1 mole) in tetrahydrofuran (25 ml). The reaction was filtered and the filtrate was partitioned between methylene chloride and water. The organic phase was separated, dried over sodium sulphate and concentrated to an oil. The oil was dissolved in ethyl acetate, treated with charcoal, filtered and again concentrated by vacuum distillation to an oil. Seed crystals were added and the oil cooled to −18°. The solid mass was stirred with petroleum ether and filtered affording 15.7 g of crude product of sufficient purity for further synthetic steps. Recrystallization from acetone/pentane afforded N-(8-quinolyl)-2-propenamide of analytical purity (m.p. 76.5°–78.5°).

Elemental analysis: calculated for $C_{12}H_{10}N_2O$: C, 72.71; H, 5.08; N, 14.13. Found: C, 72.85; H, 5.07, N, 14.11.

B. Preparation of 1-(8-Quinolyl)-2-pyrrolidinone

Potassium hydride (ca. 0.03 mole) was suspended in dry tetrahydrofuran (ca. 50 ml) under a nitrogen atmosphere at 0°. A small amount of solid trimethylsulphoxonium iodide was added to the mixture followed by a few milligrams of N-(8-quinolyl)-2-propenamide as a catalyst to speed conversion of the trimethylsulphoxonium iodide to dimethylsulphoxonium methylide. The reaction rate was followed by observing the evolution of hydrogen gas with a bubbler tube. The remaining trimethylsulphoxonium iodide (total of 3.8 g, 0.017 mole) was added as a solid and stirred at 0° until the evolution of hydrogen gas had diminished. The remaining N-(8-quinolyl)-2-propenamide (total of 3.0 g, 0.015 mole) in dry tetrahydrofuran (100 ml) was then added dropwise over 2.5 hours. The yellow-coloured mixture was stirred at room temperature for 30 hours.

The reaction was quenched with tert-butanol (ca. 2 ml). The solids were filtered and the organics evaporated to an oil. Column chromatography (ca. 200 g of SILICA GEL 60 (Trade Name)) was used to achieve separation. The solvents used were petroleum ether (0.5 g) followed by petroleum ether/acetone (50%, 6 l) and then acetone (1 l). The later fractions of petroleum ether/acetone (50%) and the early fractions from acetone elution were combined and evaporated to yield 24% 1-(8-quinolyl)-2-pyrrolidinone (m.p. 120°–121.5°).

Tlc, NMR and elemental analysis established that the compound was identical with the product of Example 1.

EXAMPLE 13

Preparation of 1-(8-Quinolyl)-2-pyrrolidinone

Pyrrolidone (8.51 g, 0.1 mole) was dissolved in dry dimethylsulphoxide (60 ml). Sodium hydride (50% suspension in mineral oil (4.79 g, 0.1 mole)) was added with stirring and the mixture was heated gently. An exotherm occurred at 80° and the mixture was cooled to give a suspension of the pyrrolidinone salt. 8-Chloroquinoline (8.18 g, 0.05 mole) was added and the mixture was heated at 100°–120° for 20 hours. Tlc (Silica gel, acetic acid/methyl cyanate 7:3) showed the disappearance of 8-chloroquinoline ($R_f$ 0.62) and a spot corresponding to 1-(8-quinolyl)-2-pyrrolidinone ($R_f$ 0.19) in addition to several other spots.

EXAMPLE A—INJECTION

| Ingredient | Amount per ampoule |
|---|---|
| 1-(8-Quinolyl)-2-pyrrolidinone | 325.0 mg |
| Sodium Chloride | 8.5 mg |
| Water for Injections, q.s. | 1.0 ml |

The finely ground active compound and sodium chloride were dissolved in the Water for Injections. The solution was filtered and sterilised by autoclaving.

combined filtrates were concentrated by vacuum distillation, ($\simeq$15 mm Hg), filtered over alumina in methylene chloride, concentrated and recyrstallized from ether/petroleum ether affording 4-chloro-N-(8-quinolyl)-butyramide. An analytical sample was prepared by recrystallization (m.p. 62°–63°), yield 53%.

Elemental analyis: Calculated. for $C_{13}H_{13}N_2OCl$: C, 62.77; H, 5.27; N, 11.27; Cl, 14.26. Found: C, 62.71; H, 5.27; N, 11.16; Cl, 14.25.

B. Preparation of 1-(8-Quinolyl)-2-pyrrolidinone

A solution of 4-chloro-N-(8-quinolyl)butyramide (2.5 g, 0.01 mole) and benzyltriethyl ammonium chloride (0.115 g, 5 mole%) in methylene chloride (30 ml) was stirred at room temperature. A solution of 30% aqueous sodium hydroxide (10 ml) was added and the mixture was stirred for 16 hours. The reaction mixture was then diluted with methylene chloride, the organic layer was drawn off and washed with a saturated salt solution, dried over sodium sulphate and evaporated to a solid residue. The residue was recrystallized from methylene chloride/petroleum ether to afford 1-(8-quinolyl)-2-pyrrolidinone which was identical by tlc and NMR in comparison with the product of Example 1, yield 90%.

EXAMPLE 4

Preparation of 1-(8-Quinolyl)-2-pyrrolidinone

4-Chlorobutryl chloride (388.0 g) was added at 40° to a solution of technical grade 8-aminoquinoline (3396.5 g) and triethylamine (278.3 g) in dimethoxyethane (2 l). After stirring overnight at ambient temperature the solids were filtered off. The filtrate was concentrated prior to additon of 13% potassium tert-butoxide in tert-butanol (2486 g) at 25°–30°. After two hours the mixture was neutralized with dilute hydrochloric acid. The slurry obtained by partial removal of the solvent was extracted three times with methylene chloride. The combined extracts were washed with water, dried over magnesium sulphate, filtered and concentrated. Ether (1 l) was added while cooling to 0°. Filtration, followed by vacuum-drying afforded 1-(8-quinolyl)-2-pyrrolidinone.

Recrystallization from acetone incorporating a DARCO G-60 (Trade Mark) activated charcoal treatment gave an 87.5% recovery of 1-(8-quinolyl)-2-pyrrolidinone as white crystals, (m.p. 122°–125°). Tlc on silica gel in chloroform/methanol, 95:5 produced one spot at $R_f 0.56$.

EXAMPLE 5

Preparation of 1-(8-Quinolyl)-2-pyrrolidinone

A mixture of $\gamma$-butyrolactone (9.5 g), technical grade 8-aminoquinoline (14.4 g), p-toluenesulphonic acid monohydrate (1.90 g) and mixed xylenes (15 ml) were refluxed with a Dean Stark trap prefilled with xylenes. After one hour $\gamma$-butyrolactone (9.0 g) was added and reflux was resumed for two hours. The residue obtained by concentration by vacuum distillation ($\simeq$15 mm Hg) of the reaction mixture was extracted with hot ethyl acetate (100 ml). The solid which formed upon cooling the ethyl acetate solution was recrystallized from acetone giving 1-(8-quinolyl)-2-pyrrolidinone, (m.p. 119°–123°), identical by tlc with the product of Example 1.

EXAMPLE 6

Preparation of 1-(8-Quinolyl)-2-pyrrolidinone

A mixture of $\gamma$-butyrolactone (4.3 g), 8-aminoquinoline (7.2 g) and zinc chloride (0.7 g) was heated at 225° for 20 hours in an autoclave. The cooled reaction mixture was partitioned between chloroform and 0.2 N hydrochloric acid. The aqueous layer was basified with sodium hydroxide then extracted with methylene chloride. Following treatment of the methylene chloride extract with FILTROL No. 1 (Trade Name) the solvent was vacuum-stripped to give 1-(8-quinolyl)-2-pyrrolidinone, identical by tlc with the product of Example 1.

EXAMPLE 7

Preparation of 1-(8-Quinolyl)-2-pyrrolidinone

A mixture of 8-aminoquinoline hydrochloride (9.0 g) and $\gamma$-butyrolactone (4.3 g) was stirred in an oil bath under nitrogen for two hours at 200°. A tarry residue containing 1-(8-quinolyl)-2-pyrrolidinone was obtained, identical by tlc with the product of Example 1.

EXAMPLE 8

Preparation of 1-(8-Quinolyl)-2-pyrrolidinone hydrochloride

A solution of 1-(8-quinolyl)-2-pyrrolidinone (3.5 g, 0.0016 mole) was prepared in 120 ml anhydrous ether by addition of methylene chloride and warming of the mixture. The solution was cooled to room temperature and treated with excess ethereal hydrochloric acid to afford a gum which crystallized on scratching. Recrystallization from an ethyl acetate/ethanol mixture afforded 1-(8-quinolyl)-2-pyrrolidinone hydrochloride, (m.p. 215°–218° decomp., with some decomposition at lower temperature), yield 61%. An analytical sample was prepared by recrystallization (m.p. 216°–220° decomp., with some decomposition at lower temperature) and was homogenous by tlc analysis.

Elemental analysis: Calculated for $C_{13}H_{13}ClN_2O$ (Mol. Wt. 248.71): C, 62.77; H, 5.27; N, 11.27. Found: C, 62.72; H, 5.26; N, 11.39. Ultraviolet $(CH_3OH)\lambda$max 215 mm (shoulder), 231 ($\epsilon 1.09 \times 10^4$), 289 ($\epsilon 2.6 \times 10^3$), 302 ($\epsilon 2.9 \times 10^3$), 314 ($\epsilon 2.5 \times 10^3$). Infrared (nujol)$\nu$max 1680 cm$^{-1}$. NMR (D$_6$-DMSO)$\delta$2.5 (m, 6H); 3.98 (t, 2H); 8.1 (m, 4H); 9.15 (m, 2H); 11.53 (s, broad, 2H).

EXAMPLE 9

Preparation of 1-(8-quinolyl)-2-pyrrolidinone

8-Aminoquinoline (2.0 g, 13.9 mmol) and 4-bromobutyronitrile (2.0 g, 13.9 mmol) were refluxed in 2-methoxyethanol (20 ml) for 24 hours under a nitrogen atmosphere. A few drops of water were added to hydrolyze the 1-(8-quinolyl)-2-iminopyrrolidinone produced, and the mixture was evaporated under vacuum. The residual oil was triturated with diethyl ether (50 ml) and decanted. Upon standing at ambient temperature the ether solution deposited 0.65 g of 1-(8-quinolyl)-2-pyrrolidinone, (m.p. 119°–121°). The ether insoluble oil was dissolved in acetone, filtered and combined with the ether liquor. The solvents were evaporated; the residue was dissolved in methylene chloride, washed with 30% aqueous sodium hydroxide and with water. The water layer was back-extracted with methylene chloride, and the combined methylene chloride layers were dried, filtered, and evaporated. The semi-